(12) United States Patent
Maier

(10) Patent No.: US 11,419,514 B2
(45) Date of Patent: Aug. 23, 2022

(54) SKIN CONTACT DETECTOR

(75) Inventor: Dieter Johann Maier, Ludmannsdorf (AT)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1124 days.

(21) Appl. No.: 13/580,314

(22) PCT Filed: Apr. 18, 2011

(86) PCT No.: PCT/IB2011/051663
§ 371 (c)(1),
(2), (4) Date: Aug. 21, 2012

(87) PCT Pub. No.: WO2011/132129
PCT Pub. Date: Oct. 27, 2011

(65) Prior Publication Data
US 2013/0030320 A1 Jan. 31, 2013

(30) Foreign Application Priority Data
Apr. 22, 2010 (EP) .................................. 10160655

(51) Int. Cl.
*A61B 5/0531* (2021.01)
*A61B 5/00* (2006.01)
*H03K 17/96* (2006.01)

(52) U.S. Cl.
CPC .......... *A61B 5/0531* (2013.01); *A61B 5/6843* (2013.01); *H03K 17/962* (2013.01); *H03K 2217/96073* (2013.01)

(58) Field of Classification Search
CPC ................ A61B 5/15; A61B 5/150007; A61B 5/150015; A61B 5/150022;
(Continued)

(56) References Cited

U.S. PATENT DOCUMENTS

| 4,940,060 | A | * | 7/1990 | Gu | A61H 39/02 128/907 |
| 5,796,355 | A | * | 8/1998 | Smigelski | 341/33 |
| 5,943,516 | A | * | 8/1999 | Uchiyama et al. | 396/281 |
| 6,647,133 | B1 | * | 11/2003 | Morita | G06K 9/00013 340/562 |

(Continued)

FOREIGN PATENT DOCUMENTS

| WO | 9701835 A1 | 1/1997 | | |
| WO | 2008129324 A1 | 10/2008 | | |
| WO | WO 2008129324 A1 | * | 10/2008 | ............. A61B 5/053 |

*Primary Examiner* — Devin B Henson
*Assistant Examiner* — H. Q. Nguyen

(57) ABSTRACT

A system for detecting skin contact comprises a signal generator (9) for generating an electric trigger signal; a reference circuit (10) comprising a capacitance ($C_{REF}$) and a resistance ($RP_{REF}$) for generating a reference signal in dependence on the trigger signal; a probe (11) touchable by a skin for measuring a skin response signal in dependence on the trigger signal; and a comparator (4) for comparing the skin response signal with the reference signal. The capacitance ($C_{REF}$) of the reference circuit (10) represents a lower bound of skin capacitance, and the resistance ($RP_{REF}$) of the reference circuit represents an upper bound of skin resistance.

20 Claims, 5 Drawing Sheets

(58) Field of Classification Search
CPC .......... A61B 5/15003; A61B 5/150038; A61B 5/150045; A61B 5/150053; A61B 5/150061; A61B 5/150068; A61B 5/150076; A61B 5/150083; A61B 5/150091; A61B 5/150099; A61B 5/150106; A61B 5/150114; A61B 5/150122; A61B 5/150129; A61B 5/01; A61B 2017/00026; A61B 2018/00875; A61B 5/04002; A61B 5/053; A61B 5/0531; A61B 5/0532; A61B 5/0533; A61B 5/0534; A61B 5/0535; A61B 5/0536; A61B 5/0537; A61B 5/0538; A61B 5/0809; A61B 5/53; A61N 1/36521
USPC ... 600/4, 206, 324, 435, 506, 536, 547, 573, 600/604; 396/281

See application file for complete search history.

(56) References Cited

U.S. PATENT DOCUMENTS

| | | | |
|---|---|---|---|
| 7,132,944 B1 * | 11/2006 | Kron | G08B 21/0288 340/572.1 |
| 2001/0022352 A1 | 9/2001 | Rudrich | |
| 2004/0021786 A1 | 2/2004 | Nakamura et al. | |
| 2005/0239075 A1 | 10/2005 | Yanagidaira et al. | |
| 2006/0055416 A1 | 3/2006 | Kinoshita et al. | |
| 2009/0028395 A1 * | 1/2009 | Riionheimo | G06F 3/04883 382/124 |
| 2009/0312666 A1 | 12/2009 | Fukumoto et al. | |

* cited by examiner

SKIN CONTACT DETECTOR

FIELD OF THE INVENTION

The invention relates to a skin contact detector. The invention further relates to a personal care appliance.

BACKGROUND OF THE INVENTION

Skin contact sensors may be used to detect presence of skin near an object. An example class of skin contact sensors is resistive skin contact sensors. Resistive contact sensors can comprise a voltage divider. In such a resistive contact sensor, the voltage drops of different resistors are compared and analyzed. However, a resistive contact sensor is fault-prone, particularly when it is used to detect skin contact.

A better choice is the use of a capacitive sensor, which evaluates and measures the capacity between two or more electrodes on the skin. The measurement of a capacity value is generally more complex than the measurement of a resistor value.

WO 2008/129324 discloses an apparatus comprising a) a set of probes each having tips arranged to simultaneously touch the skin and define a predetermined pattern on the skin, at least one of the probes being arranged to transmit a pulsed electrical signal and at least one of the probes being arranged to receive the transmitted electrical signal; b) a signal detector for detecting the or each received electrical signal; c) means for comparing a numerical value obtained from at least one detected signal from the signal detector with at least one predetermined numerical value; and d) means for providing an output when said value obtained from the detected signal differs from the predetermined numerical value by more than a predetermined amount. If the predetermined value is voltage, it is preferred that the minimum of the range be above the minimum known for skin. If the predetermined value relates to capacitance, the predetermined value is preferably based on elapsed time to reach a threshold. The means for comparing comprises a microprocessor and a storage means for storing a threshold value. The apparatus is used to control intense pulsed light devices used for local treatment of various skin conditions and to influence non-desired hair growth. The apparatus comprises a multi-channel analogue-to-digital converter (ADC) and a microprocessor.

SUMMARY OF THE INVENTION

It would be advantageous to have an improved skin contact detector. To better address this concern, a first aspect of the invention provides a skin contact detector, comprising a signal generator configured to generate an electric trigger signal;

a reference circuit comprising a capacitance and a resistance configured to generate a reference signal in dependence on the trigger signal;

a probe touchable by a skin, wherein the probe is configured to measure a skin response signal in dependence on the trigger signal; and a comparator configured to compare the skin response signal with the reference signal so as to generate a signal indicative of skin contact.

The skin response signal depends on any resistance and capacitance which is in electrical contact with the probe. When a human body touches the probe, the resistance and/or capacitance changes, and consequently, the signal measured at the probe changes. The resistance and the capacitance chosen for the reference circuit act as a simplified model of the electrical properties of the skin. Consequently, by comparing the skin response signal with the reference signal, both the capacitance and resistance of the skin are tested with the same electric circuit. This improves the reliability of the skin contact detection compared to a test of only capacitance or only resistance. Moreover, the number of electric parts is limited. A processing unit is not needed. The system may be realized with relatively simple electric parts.

The capacitance of the reference circuit may represent a lower bound of a skin capacitance, and the resistance of the reference circuit may represent an upper bound of a skin resistance. The capacitance of the skin is usually greater than the capacitance of the air surrounding the probe. Moreover, the resistance of the skin is usually lower than the resistance of the air surrounding the probe. Because of this, the capacitance at the probe increases and the resistance at the probe decreases when skin is brought in the vicinity of the probe. When the capacitance and resistance are chosen in between the corresponding values of air and skin, they can be used as threshold values to detect skin contact. The sign of the difference between the reference signal and the skin response signal may then swap when skin is brought in contact with the probe. This allows an easy detection of the skin.

The comparator may be configured to compare a voltage of the skin response signal with a voltage of the reference signal. The voltage of the signals can be compared relatively easily with low-cost parts. Moreover, the response of the voltage to a trigger signal is influenced by both capacitance and resistance. The increased capacitance causes the voltage to rise more slowly than the reference signal, which lowers the voltage compared to the reference signal, at least temporarily after the start of a trigger pulse. The lowered resistance also causes the voltage of the skin response signal to be lower. The effects caused by increased capacitance and lowered resistance are added up in the skin response signal, which may result in a substantially lower voltage of the skin response signal.

The capacitance and the resistance of the reference circuit may be arranged in parallel. This arrangement provides a model of electric properties of the human skin, because the human skin also has a capacity and a resistance in parallel. This way, the shape of the reference signal better fits the skin response signal.

The system may comprise a further reference circuit comprising a further capacitance and a further resistance configured to generate a further reference signal in dependence on the trigger signal, wherein the further capacitance represents an upper bound of skin capacitance, and wherein the further resistance represents a lower bound of skin resistance. This way, two reference signals are obtained which represent boundary cases of expected capacity and resistance values in case of skin contact. This improves the detection, as it enables to distinguish skin contact from contact with a highly conductive material or a very high-capacity object.

The system may comprise a further comparator configured to compare the skin response signal with the further reference signal, and an output signal generator for generating an output indicating whether the skin response signal is in between the reference signal and the further reference signal. The two reference signals may represent upper and lower bounds of the skin response signal (for example, a voltage) in case of skin contact. This can be efficiently handled using the further comparator and the output signal generator.

The electric trigger signal may comprise a periodic pulse signal. Such a periodic pulse generates a reference signal and a skin response signal having a slope which depends on the capacity and a convergence value which depends on the resistance. This allows both properties to be compared simultaneously and with one circuit. Moreover, the periodicity allows to test the slope (i.e., the capacity) at regular time intervals. An example of the periodic pulse signal is a clock signal.

The system may comprise a further probe touchable by the skin and configured to measure a further skin response signal in dependence on the trigger signal at a different spot of the skin, and a further comparator configured to compare the further skin response signal with the reference signal, and an output signal generator configured to generate a skin touch output in dependence on the output of the comparator and the further comparator. This provides a more reliable measurement. Moreover, it allows to test whether an area in between the probe and the further probe is close to the skin. This way, more accurate positioning of a device having the skin contact sensor can be realized.

The system may further comprise a surface arranged for being held by a hand, wherein a ground is configured to enable electric communication with the hand when the hand holds the surface. This is a convenient way of providing a ground. No separate ground probe is necessary. For example the ground may be arranged for enabling a capacitive connection with the hand through the surface.

The system may further comprise a housing, wherein the surface comprises at least part of an outer surface of the housing. This is a convenient arrangement, for example for hand-held appliances, which may be held by gripping the surface of the appliance. It may also be used for larger appliances, which may comprise a grip element or a touchable surface, for example.

The probe may comprise a conductive material protruding from a housing. This arrangement facilitates contact of the probe with the skin surface.

The system may further comprise a switch operatively coupled with the comparator and configured to control an action having an impact on the skin in dependence on an output of the comparator. This way, the action can be made conditional on a proper positioning of the skin. This may increase the safety.

The system may further comprise a source of electromagnetic pulses or light, wherein the switch is configured to control the source of electromagnetic pulses or light. This way, the pulses or light may be inhibited when there is no contact with the skin detected. The source of light may comprise a source of laser light.

Another aspect of the invention provides a personal care appliance comprising a system for detecting skin contact as set forth. This allows the operation of the personal care appliance to be controlled in dependence on the presence of a valid skin contact.

BRIEF DESCRIPTION OF THE DRAWINGS

These and other aspects of the invention are apparent from and will be elucidated with reference to the embodiments described hereinafter. In the drawings.

DETAILED DESCRIPTION OF EMBODIMENTS

In this description, inter alia, a skin contact sensor solution is disclosed which makes use of both resistive and capacitive properties of the skin to improve the skin contact detection reliability. Moreover, a relatively small number of electrical parts is used. Both measurement principles can be evaluated by the same electrical circuit. In the prior art, normally two (or more) different interpretation circuits have to be implemented to measure the resistance and the capacitive changes of the contact sensor.

The skin contact sensor may comprise a resistive reference element and a capacitive reference element. These elements may be compared with a skin contact element by a comparing element. The reference element and the skin contact element may be powered by a periodic trigger signal, for example a clock (CLK) or pulse-wide-modulation (PWM) signal (which can be easily provided by a microcontroller or by other means).

The outputs of the reference element and the skin contact sensor may be compared by a simple comparing element such as a comparator, an operational amplifier, or directly by a microcontroller. The voltage drops of the resistive reference element and the skin contact element depends on the resistance (and on the amplitude of the trigger signal).

In addition to the resistive evaluation, also the capacitive behavior of the skin contact sensor may be compared with the capacitive reference element. To that end, the same comparing element can be used to measure the difference between the time constants of the skin contact sensor and the capacitive reference element. Due to the fast transient behavior of the used CLK or PWM signal, the capacitive value can be evaluated by measuring the voltage difference between the transient response voltages of the reference element and the skin contact element. If the capacitive value of the skin contact sensor is higher than the capacitive value of the reference element, the time constant of the skin contact element is higher than the one from the reference element. In this case, voltage of the skin contact element will be temporarily lower than the voltage of the reference element, which can be detected by the comparator.

Because a resistive and capacitive reference element may be used, the calibration of the skin contact sensor can be done by setting the resistance and capacity of the reference elements. This way, different "skin contact detection scenarios" can be achieved (for example: full contact, partial contact, valid contact only with body cream, valid contact only with wet skin, valid contact only with dry skin, . . . ).

Figure 1:
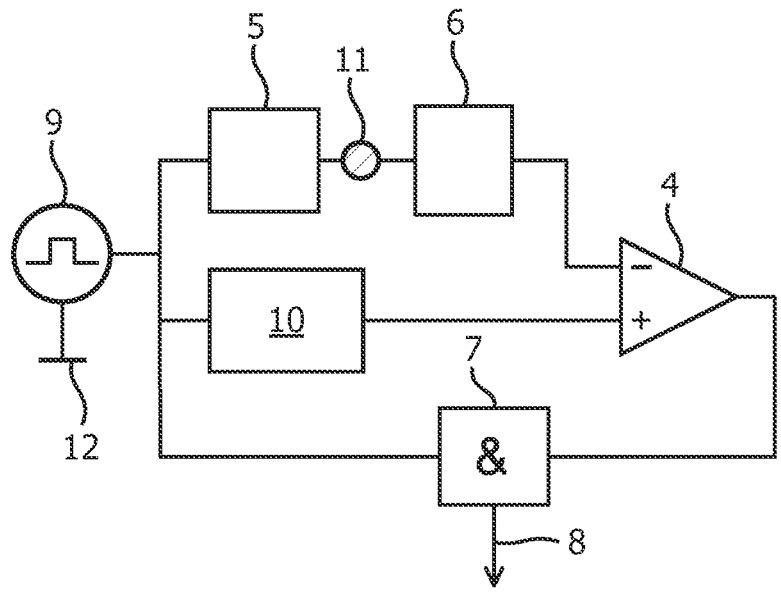
FIG. 1 is a block diagram of an embodiment of a system for detecting skin contact.

FIG. 1 illustrates a system for detecting skin contact, or a skin contact detector. The system comprises a probe 11 touchable by a skin for measuring a skin response signal. The system further comprises a signal generator 9 for generating an electric trigger signal. This trigger signal may comprise a step function, for example from zero volt to +5 volt. Any other trigger signal can be used. A non-constant trigger signal is advantageous for measuring capacity.

The signal generator 9 is operatively connected to the probe 11. Consequently, the skin response signal depends on the trigger signal. The signal generator 9 may be further operatively connected to a reference circuit 10 comprising a capacitance and a resistance for generating a reference signal in dependence on the trigger signal. Additional circuitry 5 may be provided between the signal generator 9 and the probe 11. The probe 11 and the reference circuit 10 are operatively connected to a comparator 4. The comparator 4 compares the skin response signal with the reference signal. Some additional circuitry 6 may be provided between the probe 11 and the comparator 4. The output of the comparator may be indicative of skin contact. To further improve the skin contact detection, an AND gate 7 may have as inputs the output of the comparator and of the signal generator. This allows to take only relevant portions of the signal into account in the output signal 8. The function of the AND gate may be provided by a microcontroller, for example. The capacitance of the reference circuit 10 may represent a lower bound of skin capacitance. The resistance of the reference circuit 10 may represent an upper bound of skin resistance. The ground 12 may be implemented as a further probe which is also touched by the skin in case of skin contact.

Figure 2:
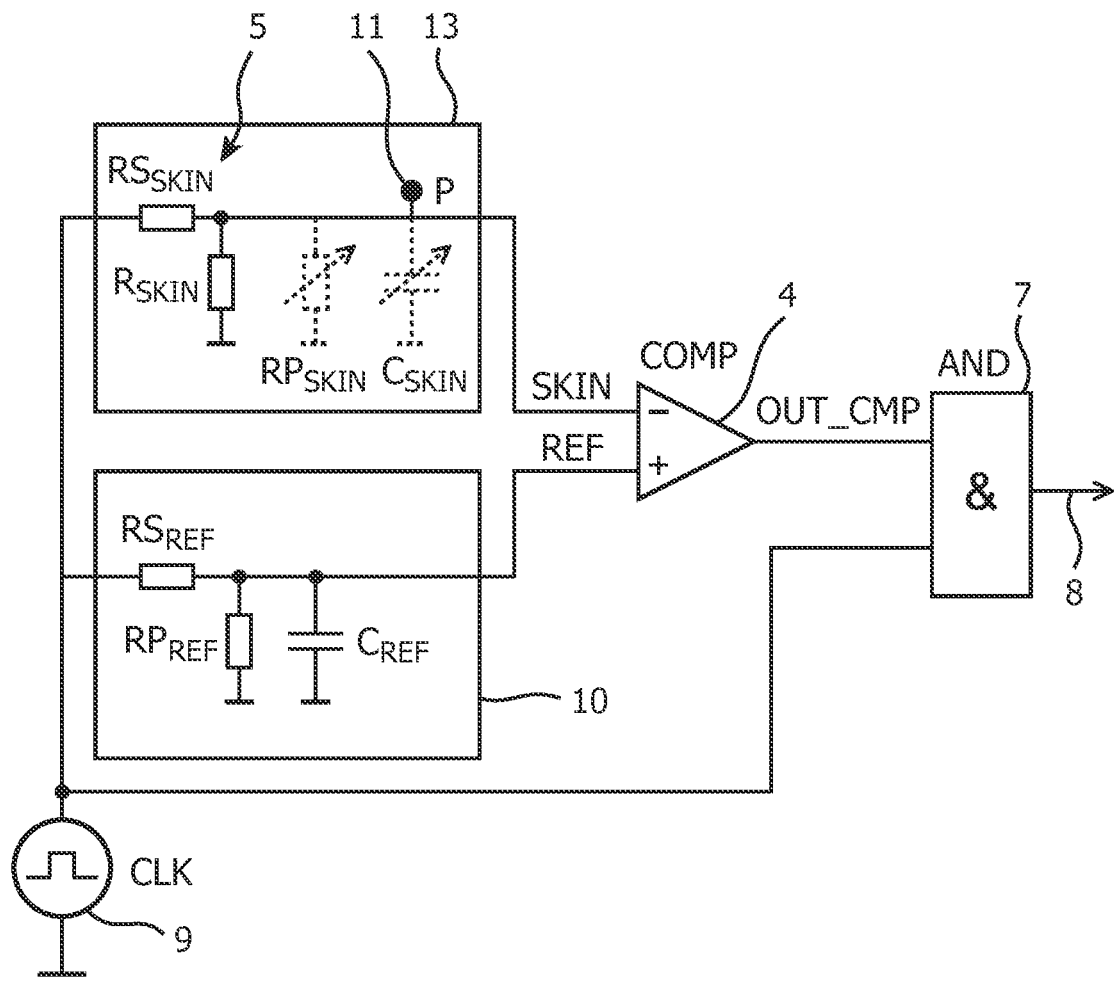
FIG. 2 is a block diagram of a further embodiment of a system for detecting skin contact.

FIG. 2 illustrates a more detailed example of the system for detecting skin contact. Similar items have been labeled with the same reference numerals across the figures. The reference circuit 10 comprises a resistance $RP_{REF}$ in parallel to the capacitance $C_{REF}$. Another resistance $RS_{REF}$ is arranged in series with the resistance $RP_{REF}$ and the capacitance $C_{REF}$. In this example, the additional circuitry 5 comprises a voltage divider comprising resistance $RS_{SKIN}$ and resistance $R_{SKIN}$, the latter resistance $R_{SKIN}$ being connected to ground and the probe being arranged in between the resistance $RS_{SKIN}$ and resistance $R_{SKIN}$. As indicated in the drawing by means of dashed objects, the skin connected to the probe may behave electrically as a variable resistance $RP_{SKIN}$ and parallel variable capacity $C_{SKIN}$. As described with reference to FIG. 1, the capacitance $C_{REF}$ of the reference circuit 10 may represent a lower bound of skin capacitance, and the resistance $RP_{REF}$ of the reference circuit 10 may represent an upper bound of skin resistance. The comparator 4 is arranged for comparing a voltage of the skin response signal with a voltage of the reference signal. The resulting signal OUT_COMP and the output of the signal generator 9 may be combined, for example in an AND gate 7, to obtain the final output signal 8.

Two probes may be provided, one probe is skin contact probe 11 and the other probe is connected to the ground. This is true for both FIG. 1 and FIG. 2. However, this is not a limitation, as will be described elsewhere in this description. Both probes may be arranged beside each other, such that both probes can make electrical contact when a skin touches the probes.

The skin contact sensor and the reference element are supplied by a trigger signal, to obtain a transient response of the reference element and the skin contact sensor. Two main signal parameters may be observed in the signal obtained from the skin contact element 11:

$\Delta U_{SKIN}$: Voltage drop to ground according to the resistance of the skin ($RP_{SKIN}$).

$\Delta \tau_{SKIN}$: Transient response rise time according to the capacity of the skin ($C_{SKIN}$).

Corresponding signals may be observed in the signal obtained from the reference circuit 10:

$\Delta U_{REF}$: Voltage drop to ground according to the resistance ($RP_{REF}$) of the reference element 10.

$\Delta \tau_{REF}$: Transient response rise time according to the capacity ($C_{REF}$) of the reference element 10.

The output of the comparing element 4 is "low" as long as the skin values ($\Delta U_{SKIN}$, $\Delta \tau_{SKIN}$) are higher than the reference values ($\Delta U_{REF}$, $\Delta \tau_{REF}$). The output of the comparing element 4 is "high" as long as the skin values ($\Delta U_{SKIN}$, $\Delta \tau_{SKIN}$) are lower than the reference values ($\Delta U_{REF}$, $\Delta \tau_{REF}$). However, this is not a limitation. For example, the meaning of the "high" and "low" states may be swapped by swapping the connections of the comparator with the skin contact probe 11 and the reference circuit 10.

The reference element comprising a defined series resistor ($RS_{REF}$) and a defined capacity ($C_{REF}$) may form a low pass filter with a defined transient response rise time ($\Delta \tau_1 REF$) from the CLK signal. This transient response rise time may be compared with the variable transient response rise time ($\Delta \tau_{SKIN}$) of the low pass filter which is formed by the defined series resistor ($RS_{SKIN}$) and the variable capacity ($C_{SKIN}$) from the same CLK signal. Here, the variable capacity ($C_{SKIN}$) refers to the capacity of a body (skin) in contact or very close to the probe 11. This is variable because the capacity ($C_{SKIN}$) depends on whether skin is in contact with the probe, and it moreover depends on the properties of the skin, and on anything on the skin (such as water or a gel). The different response times may be detected by the comparator because there will be an at least temporary voltage difference associated with a different rise time.

The additional defined parallel resistor ($RP_{REF}$) may cause together with the defined serial resistor $RS_{REF}$ a specific reference potential difference ($\Delta U_{REF}$). The skin also has a (variable) resistance $RP_{SKIN}$ which, together with the serial resistor $RS_{SKIN}$, causes a variable potential difference ($\Delta U_1 SKIN$) which may be compared with the reference potential difference ($\Delta U_{REF}$). The difference in rise time and potential difference caused by the capacity and resistance of the skin add up to an increased difference between the voltage associated with skin contact and the voltage with no skin contact.

As long as the voltage value on the negative input of the comparator (SKIN) is higher than the voltage value of the positive input (REF), the output of the comparator (OUT_CMP) is on the value "low" (This is the case when $RP_{SKIN}$ is higher than $RP_{REF}$ and/or $C_{SKIN}$ is lower than $C_{REF}$). If the voltage value the negative input of the comparator (SKIN) is lower than the voltage value of the positive input (REF), the output of the comparator (OUT_CMP) switches to the value "high" (This is the case when $RP_{SKIN}$ is lower than $RP_{REF}$ and/or $C_{SKIN}$ is higher than $C_{REF}$). However, this is only an example arrangement. The SKIN and REF signals can be exchanged, which would lead to negation of the signals and swap of "high" and "low" situations.

When the electrical circuit is in its normal working operation, the skin contact probe 11 as well as the reference circuit 10 may be supplied by the same CLK signal. The electronic parts of the reference circuit 10 (in the example of FIG. 2, $RS_{REF}$, $RP_{REF}$ and $C_{REF}$) cause a defined resistive voltage drop ($\Delta U_1 REF$) and a defined transient rise time behavior ($\Delta \tau_1 REF$). Although the electronic parts of the skin contact circuit 13 ($RS_{SKIN}$, $R_{SKIN}$, $RP_{SKIN}$ and $C_{SKIN}$) may cause a resistive voltage drop ($\Delta U_1 SKIN$) and a transient rise time behavior ($\Delta \tau_1 SKIN$). The values $RP_{SKIN}$ and $C_{SKIN}$ are variable and are defined by the skin. If there is no skin contact between the probe 11 and ground (GND), the additional value of $RP_{SKIN}$ is very high (=open) and the additional capacity $C_{SKIN}$ is very low (=low specific dielectric).

Figure 3:
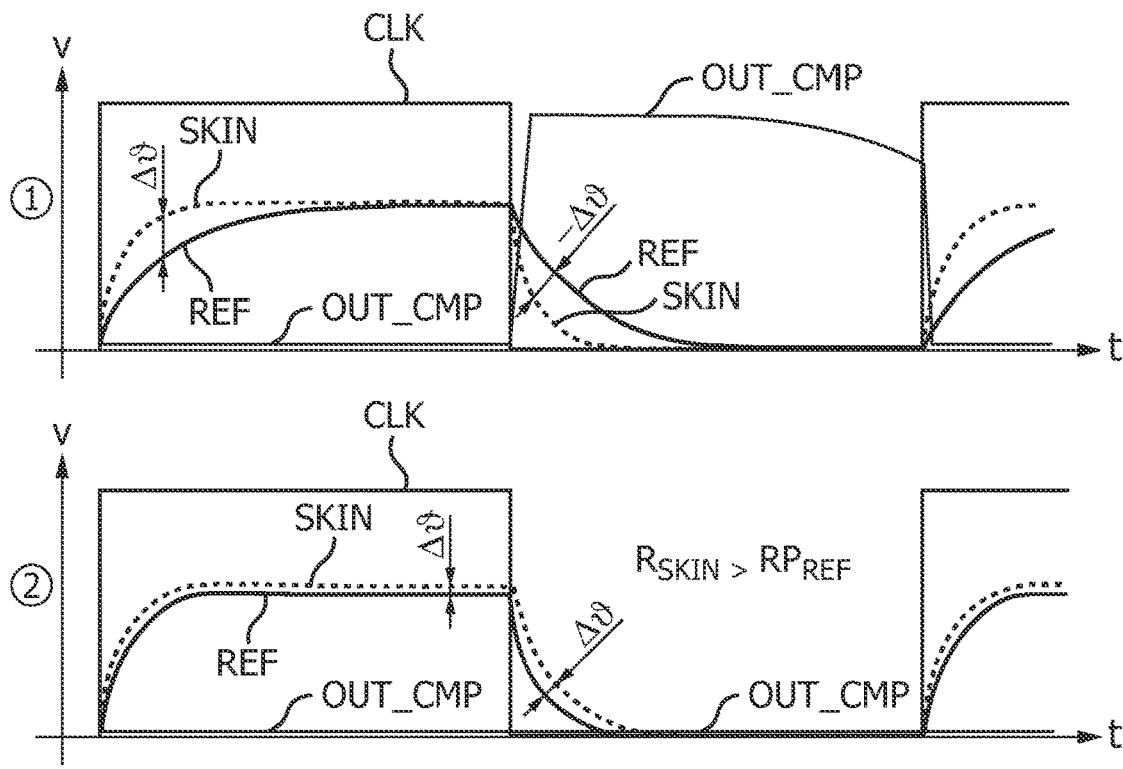
FIG. 3 shows graphs of signals in case of no valid skin contact detection.

FIG. 3 shows two graphs illustrating the voltage effect if skin contact is not valid. Note that the graphs are only sketches and are not drawn to scale. In particular, the scale of the different graphs is not the same. The top graph of FIG. 3 shows an example of transient signal behavior of the reference element and the skin contact sensor. As long as there is no valid skin contact, $C_{SKIN}$ is very low and so the transient rise time of the skin contact sensor (SKIN) is lower than the transient rise time of the reference element (REF). The voltage difference (ΔU) between the comparator inputs cause a negative (=low) output (OUT_CMP) because the voltage of the skin contact sensor is higher than the voltage of the reference element during the clock pulse. The AND gate 7 discards the difference signal when there is no clock pulse.

The bottom graph of FIG. 3 shows a sketch of exemplary resistive signal behavior of the reference element and the skin contact sensor. As long as there is no valid skin contact, $RP_{SKIN}$ is very high and so the output voltage of the skin contact sensor (SKIN) is higher than the output voltage of the reference element (REF). The voltage difference (ΔU) between the comparator inputs cause a negative (=low) output (OUT_CMP) because the voltage of the skin contact sensor is higher than the voltage of the reference element. If the CLK signals changes to the low state, there is still a positive voltage difference between the comparator inputs so that the comparator output (OUT_CMP) keep staying on the negative (=low) value.

Figure 4:
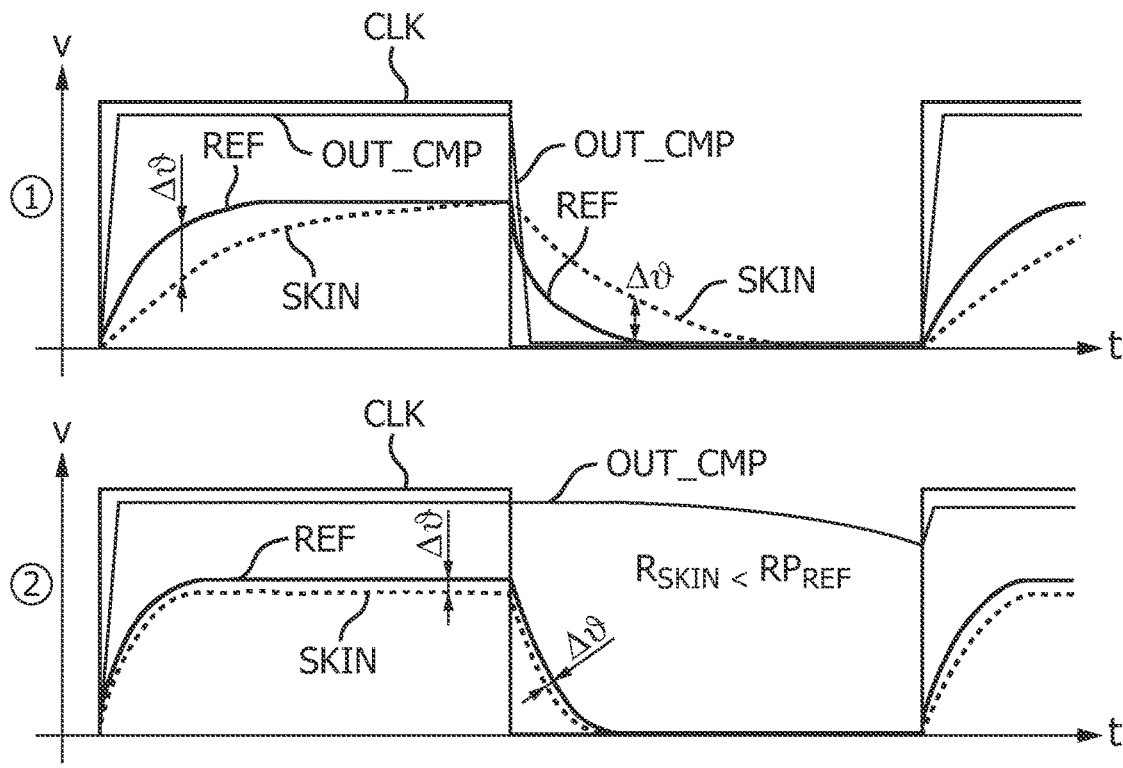
FIG. 4 shows graphs of signals in case of valid skin contact detection.

FIG. 4 shows graphs corresponding to the case that skin contact is valid, i.e., there is skin in contact with the probe 11. Note that the graphs are only sketches and are not drawn to scale. In particular, the scale of the different graphs is not the same. The top graph of FIG. 4 shows a sketch of exemplary transient signal behavior of the reference circuit (REF) and the skin contact circuit (SKIN). When there is a valid skin contact, $C_{SKIN}$ is higher than when there is no valid skin contact. $C_{REF}$ may be chosen such that $C_{SKIN}$ is higher than $C_{REF}$ in case of skin contact. Consequently, the transient rise time of the skin contact circuit (SKIN) is longer than the transient rise time of the reference element (REF). The negative voltage difference (−ΔU) between the comparator inputs causes a positive (=high) output (OUT_CMP) of the comparator because the voltage of the skin contact circuit is lower than the voltage of the reference circuit. Although the end of the clock pulse may be the start of a transient fall time wherein the voltage of the skin contact circuit (SKIN) is higher than the voltage of the reference circuit (REF), the effect of this on the output of the comparator may be discarded by means of the AND gate 7.

The bottom graph of FIG. 4 shows a sketch of resistive signal behavior of the reference element and the skin contact sensor. When there is a valid skin contact, $RP_{SKIN}$ is lower than when there is no skin contact. In particular, the resistance $RP_{REF}$ in the reference circuit may be chosen such that the output voltage of the skin contact sensor (SKIN) is lower than the output voltage of the reference element (REF) in case of skin contact. The negative voltage difference (−ΔU) between the comparator inputs causes a positive (=high) output (OUT_CMP) of the comparator because the voltage of the skin contact sensor is lower than the voltage of the reference element. If the CLK signal changes to the low state, there may still be a negative voltage difference between the comparator inputs so that the comparator output (OUT_CMP) stays on the positive (=high) value. It depends on the capacitive discharge behavior of the reference element how long the OUT_CMP value will stay on the high level. In the diagram can be seen that the OUT_CMP value is slightly decrease its voltage level. However, this may be irrelevant if the AND gate 7 is applied.

The AND gate 7 can be a separate electronic part. It can also be implemented on a microcontroller, PGA, FPGA, logic array, or otherwise. If the skin contact is valid, the output of the AND gate (OUTPUT) may have nearly the same behavior as the clock signal. The skin contact is valid when the capacity of the skin contact sensor is higher and/or the resistance of the skin contact sensor is lower than the capacity and resistor values of the reference element. If the skin contact is not valid, the OUTPUT signal is constant on the value low.

The calibration of the skin contact sensor may allow different "skin contact scenarios" to be achieved. For example, skin contact may only be validly detected in case of any one of: full contact, partial contact, valid contact only with body cream on the skin, valid contact only with wet skin, valid contact only with dry skin. This calibration can be performed by adjusting or exchanging the electronic parts of the reference circuit ($RS_{REF}$, $RP_{REF}$ and $C_{REF}$). To this end, the electronic parts of the reference circuit may be variable. In addition, or alternatively, a plurality of reference circuits 10 and corresponding comparators 4 may be realized, each calibrated to a different one of these scenarios, to support generate different control signals in case of different kinds of skin contact.

A plurality of reference circuits 10 and corresponding comparators 4 may also be used to improve the skin contact detection. For example, to avoid a valid skin contact signal when the skin contact sensor is for example exposed to a very high capacity or low ohmic surface. Such a situation could also arise when the skin contact is covered with water or shorted.

Figure 5:
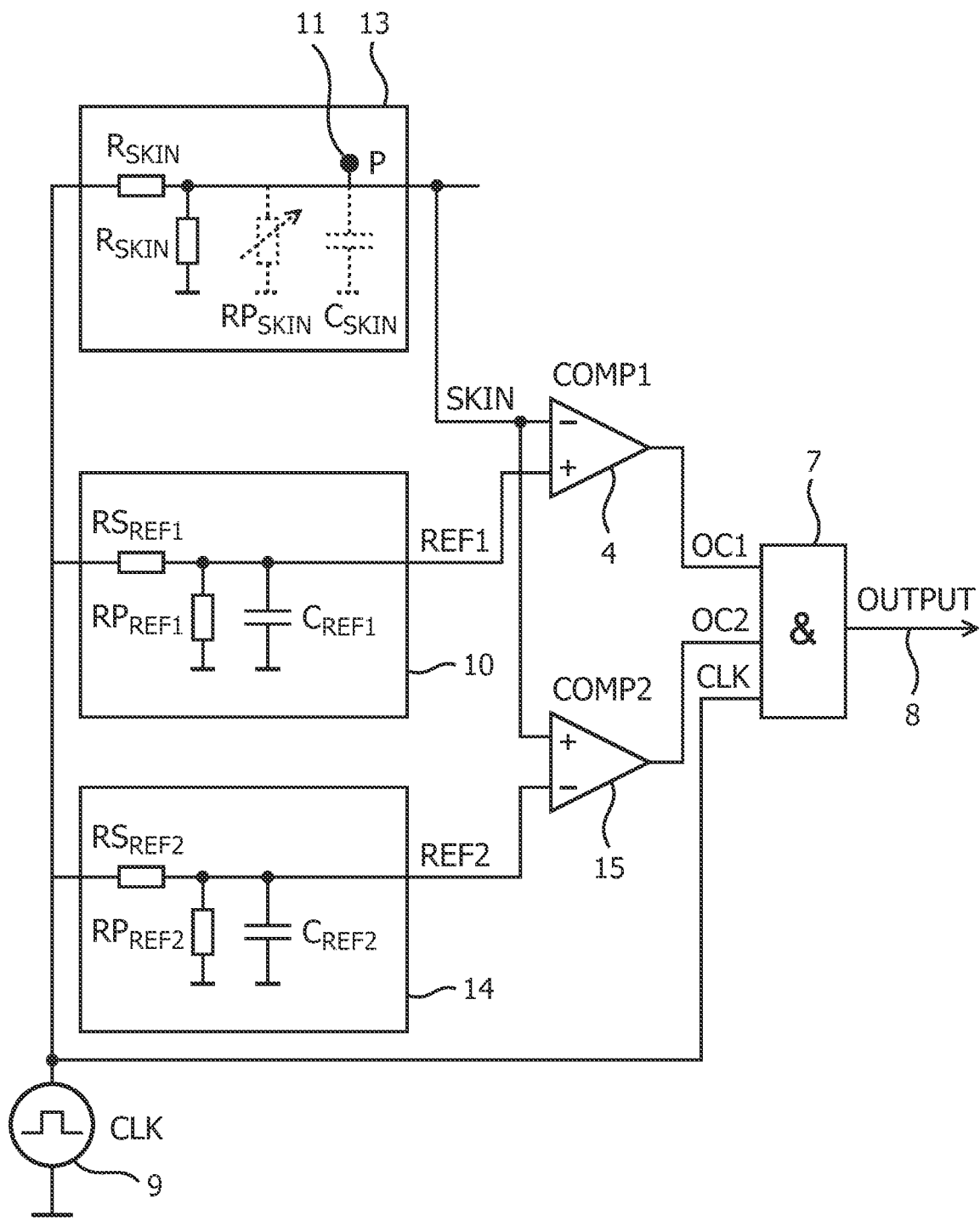
FIG. 5 is a block diagram of an embodiment comprising two reference circuits.

FIG. 5 shows a block diagram of a system for detecting skin contact. As noted before, similar items have been indicated with the same reference numerals throughout the figures. The skin contact circuit 13 and the reference circuit 10 and the comparator 4 are similar to the ones described for FIG. 2. The electric parts of the reference circuit 10 have been indicated with subscript 1 for clarity. The system of FIG. 5 also comprises a further reference circuit 14 comprising a further capacitance ($C_{REF2}$) and a further resistance ($RP_{REF2}$) for generating a further reference signal in dependence on the trigger signal, which may be a clock signal of the clock 9. As described above, this further reference circuit 14 may be used in different applications, to be able to detect multiple contact scenarios or to improve the quality of the detection. In the arrangement of FIG. 5, the system detects whether the signal of the skin contact circuit 13 is in between the reference signals of the two reference circuits. However, this is not a limitation. Other arrangements of the comparators 4 and 15 and of the output signal generator 7 are also possible. In the present arrangement, the further capacitance ($C_{REF2}$) represents an upper bound of skin capacitance, and the further resistance ($RP_{REF2}$) represents a lower bound of skin resistance. The system comprises a further comparator 15 for comparing the skin response signal (SKIN) with the further reference signal (REF2). The system further comprises an output signal generator 7 for generating an output indicating whether the skin response signal is in between the reference signal and the further reference signal.

As shown in the figure, the output signal generator 7 can be an AND gate. However, this is not a limitation. The additional reference circuit may define the lowest allowed skin resistance ($RP_{REF2}$) and the maximal allowed skin capacitance ($C_{REF2}$). If the skin resistance becomes smaller than the $RP_{REF2}$ value or the skin capacity exceeds the $C_{REF2}$ value, the output of comparator 15 (COMP2) falls to the value low and the output (OUTPUT) of the AND-gate go to the value low. To this end, the further reference circuit 14 is coupled to the negative input of the further comparator 15. However, this is not a limitation. It is also possible to connect the further reference circuit 14 to the positive input. This can be used to implement other functionality. Moreover, it can be corrected by a properly configured output signal generator 7.

Figure 6:
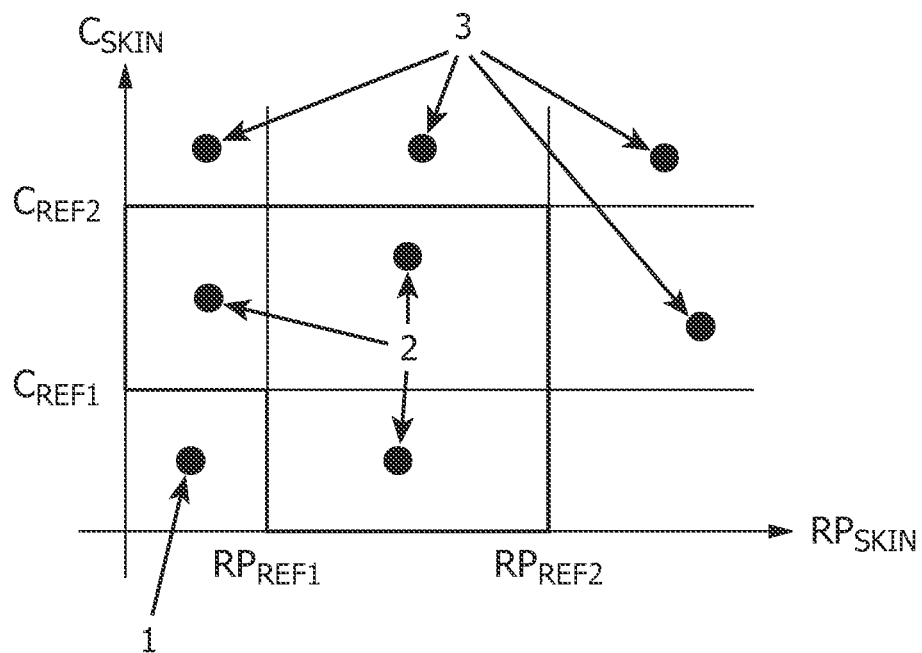
FIG. 6 is a state diagram corresponding to FIG. 5.

FIG. 6 illustrates a sketch of a "valid state diagram" of the skin detection circuit shown in FIG. 5. The horizontal axis represents the skin resistance ($RP_{SKIN}$) and the vertical axis represents the skin capacity ($C_{SKIN}$). As can be seen, $C_{REF2} > C_{REF1}$ and $RP_{REF1} > RP_{REF2}$. If $C_{SKIN}$ is lower than $C_{REF}$ and/or $RP_{SKIN}$ is higher than $RP_{REF1}$, the output of the skin detection circuit is "not valid" or "low" (state 1 in the figure). If $C_{SKIN}$ is higher than $C_{REF2}$ and lower than $C_{REF2}$ and/or $RP_{SKIN}$ is lower than $RP_{REF1}$ and higher than $RP_{REF2}$, the output of the skin detection circuit is "valid" or "high" (state 2 in the figure). If $C_{SKIN}$ is higher $C_{REF2}$ and/or $RP_{SKIN}$ is lower than $RP_{REF2}$, the output of the skin detection circuit is "not valid" or "low" (state 3 in the figure).

Figure 7:
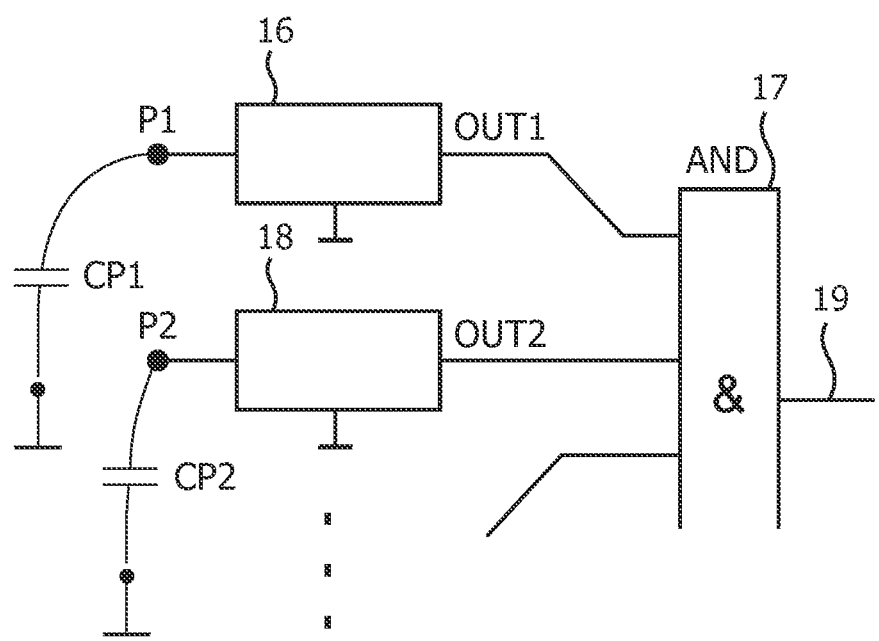
FIG. 7 is a block diagram of an embodiment comprising multiple skin contact probes.

FIG. 7 shows a simplified diagram of a skin contact detector comprising a probe P1 and a further probe P2 both touchable by a skin for measuring a skin response signal in dependence on the trigger signal. These probes P1 and P2 may be arranged next to each other on the surface of an appliance to probe two or more different spot of the skin. Probe P1 is connected to circuitry 16 and probe P2 is connected to circuitry 18. These circuitries 16 and 18 may have a structure similar to what is shown in FIG. 2, with a comparator 4 for comparing the skin response signal with the reference signal. These circuitries may have separate reference circuits or may share the same reference circuit. The output signals OUT1 and OUT2 of the circuitries 16 and 18 may correspond to OUT_CMP or to output signal 8 of FIG. 2. The output signals OUT1 and OUT2 are combined in the output signal generator 17 which may be an AND gate, to obtain the output skin contact signal 19.

The skin contact detector in this case comprises more than one skin contact probes P1, P2, . . . . It is possible to extend this system to more than two probes P1, P2, as is illustrated in the figure. The skin contact probes may have circuitry 16,18 connected therewith to detect any skin contact. The resulting signals (OUT1, OUT2, . . . ) of each of the skin contact probes (P1, P2, . . . ) are combined in output signal generator 17. Output signal generator 17 may comprise an AND gate, as shown, which only outputs a valid skin contact signal if each individual probe's resulting signal (OUT1, OUT2, . . . ) is indicative of valid skin contact. CP1 and CP2 represent the capacitive connection with the ground of the skin contact detection system via the skin. The ground may be connected to a further probe or may be implemented differently, as explained in the following example.

Figure 8:
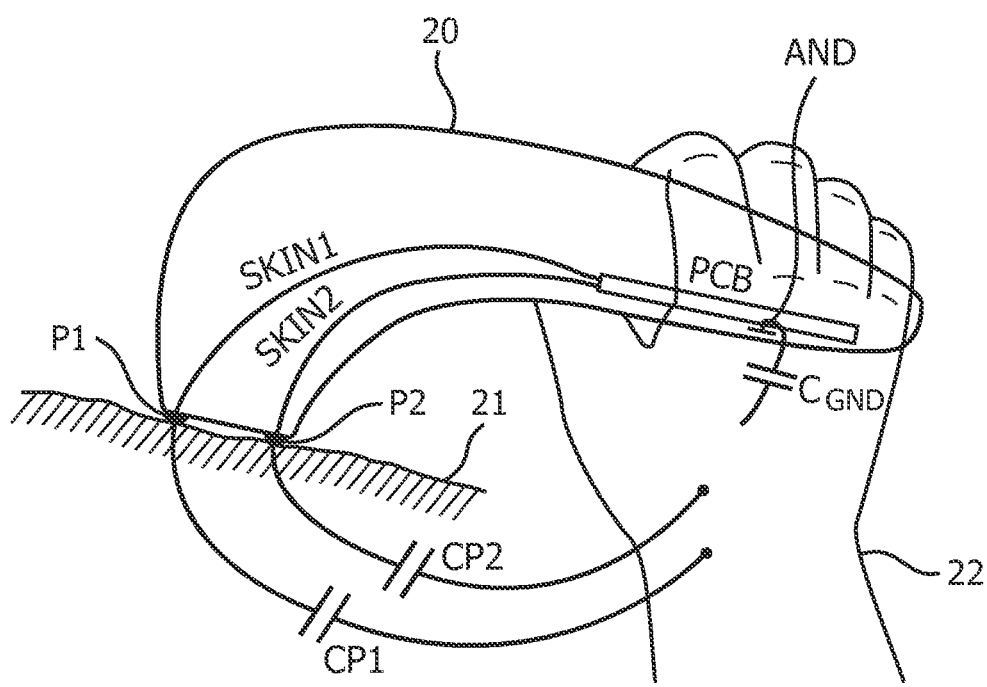
FIG. 8 is a sketch of a home care device in use.

FIG. 8 illustrates a skin contact sensor in use in a personal care appliance 20. The personal care appliance 20 comprises two probes P1, P2 touching a skin surface 21, for example facial skin. The touched portion of the skin 21 is in electrical contact with the hand 22 of the same person, as is schematically represented by capacities CP1 and CP2 ("strew capacities"). The probes P1 and P2 are connected to circuitry for detecting the skin contact, as described above. This circuitry is in this example implemented on a printed circuit board (PCB), as shown. The ground (GND) of the skin contact sensor may be connected to the manifold housing of the personal care appliance 20 and makes an at least capacitive connection with the hand 22, as is schematically indicated by the symbol $C_{GND}$. The housing may be made of a non-conductive material. The housing thus comprises a surface for being held by a hand, to hold the personal care appliance 20, wherein a ground is connected to the surface. In general, the ground is arranged for enabling electric communication, for example by means of capacitive connection, with the hand when the hand holds the surface.

The probes P1 and P2, as shown, may protrude from the housing. The probes may also be non-protruding. They may also comprise a conductive material. The ground may, instead of being implemented via a grip surface as in FIG. 8, also be implemented as a probe made of a conductive material, similar to P1 and P2.

In general, the system for detecting skin contact may be used to control operation of an appliance. For example, a switch may be operatively coupled with the comparator for controlling an action of the appliance, such as generating a light signal or an auditive signal. The action may have an impact on the skin, to perform a skin treatment, for example. The system for detecting skin contact may be used to control a source of electromagnetic pulses or light, by means of a switch.

The described systems can be used whenever a full, partial, or special kind of skin contact needs to be detected. For example, it can be used in skincare appliances. Such a skincare appliance may comprise a source of high power flash light (or in general a source of electromagnetic pulses or lights), or a source of high power laser light. Such a source may be controlled using the output of the skin contact sensor. For example, skin contact detector may be used as a safety measure. The source of energy may be activated only in case skin contact is detected.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A skin contact detector for detecting contact of a probe with skin, the skin contact detector comprising:
   a signal generator configured to generate an electric trigger signal;
   a reference circuit including a capacitance ($C_{REF}$) and a resistance ($RP_{REF}$) configured to represent a model capacitance and resistance properties of the skin to be contacted by the probe, said reference circuit being adapted to produce a reference signal at a reference output of the reference circuit in response to the trigger signal being applied by the signal generator to a reference input of the reference circuit;
   a skin contact circuit adapted to produce a skin response signal at a skin contact output of the skin contact circuit in response to the trigger signal being applied by the signal generator to a skin contact input of the contact circuit, said skin response signal being representative of any variations of a skin capacitance and a skin resistance electrically applied by the probe to the skin contact circuit; and a comparator adapted to compare the skin response signal at the skin contact output of the skin contact circuit with the reference signal at the reference output of the reference circuit and to generate a predetermined output signal indicating skin contact by the probe when at least one of:

(i) the skin response signal simultaneously indicates the skin capacitance of the skin contact circuit is larger than the capacitance ($C_{REF}$) of the reference circuit and the skin resistance of the skin contact circuit is smaller than the resistance ($RP_{REF}$) of the reference circuit, or (ii) the skin response signal simultaneously indicates the skin capacitance is smaller than the capacitance ($C_{REF}$) of the reference circuit and the skin resistance of the skin contact circuit is larger than the resistance ($RP_{REF}$) of the reference circuit.

2. The skin contact detector according to claim 1, wherein:

the capacitance ($C_{REF}$) of the reference circuit represents a lower bound of skin capacitance; and the resistance ($RP_{REF}$) of the reference circuit represents an upper bound of skin resistance.

3. The skin contact detector according to claim 1, wherein the comparator is configured to compare a voltage of the skin response signal with a voltage of the reference signal.

4. The skin contact detector according to claim 1, wherein the capacitance ($C_{REF}$) and the resistance ($RP_{REF}$) of the reference circuit are electrically connected in parallel.

5. The skin contact detector according to claim 1, wherein the electric trigger signal is a periodic pulse signal.

6. The skin contact detector according to claim 1, further comprising a surface arranged for being held by a hand, wherein a ground is configured to enable electric communication with the hand when the hand holds the surface.

7. The skin contact detector according to claim 6, wherein the ground is configured to make a capacitive connection with the hand through the surface.

8. The skin contact detector according to claim 6, further comprising a housing and said surface including at least part of an outer surface of the housing.

9. The skin contact detector according to claim 1, further comprising a housing and said probe including an electrically conductive member protruding from the housing.

10. The skin contact detector according to claim 1, wherein said skin contact detector is further configured to control an action having an impact on the skin in dependence on the output signal of the comparator.

11. The skin contact detector according to claim 10, further comprising at least one source of electromagnetic pulses and a source of light controlled in dependence on the output signal of the comparator.

12. The skin contact detector according to claim 1, further comprising:

an output signal generator adapted to produce an output indicating whether the comparator is generating the predetermined output signal indicating skin contact by the probe.

13. The skin contact detector according to claim 12, wherein the output signal generator produces the output in response to the trigger signal being applied by the signal generator to the output signal generator.

14. A skin contact detector for detecting contact of a probe with skin, said skin contact detector comprising:

a signal generator configured to generate an electric trigger signal;

a first reference circuit including a first capacitance ($C_{REF1}$) and a first resistance ($RP_{REF1}$) configured to represent a first model of capacitance and resistance properties of the skin to be contacted by the probe, said first reference circuit being adapted to produce a first reference signal at a first reference output of the first reference circuit in response to the trigger signal being applied by the signal generator at a first reference input of the first reference circuit;

a second reference circuit including a second capacitance ($C_{REF2}$) and a second resistance ($RP_{REF2}$) configured to represent a second model of capacitance and resistance properties of the skin to be contacted by the probe, said second reference circuit being adapted to produce a second reference signal at a second reference output of the second reference circuit in response to the trigger signal being applied by the signal generator at a second reference input of the second reference circuit;

wherein the first capacitance ($C_{REF1}$) and the second capacitance ($C_{REF2}$) define a range of skin capacitances indicative of skin contact by the probe;

wherein the first resistance ($RP_{REF1}$) and the second resistance ($RP_{REF2}$) define a range of skin resistances indicative of skin contact by the probe;

a skin contact circuit adapted to produce a skin response signal at a skin contact of the skin contact circuit in response to the trigger signal being applied by the signal generator at a skin contact input of the skin contract circuit, said skin response signal being representative of any variations of a skin capacitance and a skin resistance electrically applied by the probe to the skin contact circuit; and a comparator arrangement adapted to compare the skin response signal at the skin contact output of the skin contact circuit with the first reference signal at the first reference output of the first reference circuit and with the second reference signal at the second reference output of the second reference circuit and to generate an output signal indicating skin contact by the probe when said probe is moved to a position where the skin capacitance represented by the skin response signal lies between the first capacitance of the first reference circuit and the second capacitance of the second reference circuit simultaneous with the skin resistance represented by the skin response signal lying between the first resistance of the first reference circuit and the second resistance of the skin reference circuit.

15. The skin contact detector according to claim 14, wherein the comparator arrangement comprises:

a first comparator configured to compare the skin response signal with the first reference signal;

a second comparator configured to compare the skin response signal with the second reference signal; and an output signal generator configured to generate an output indicating whether a magnitude of the skin response signal is in between a magnitude of the first reference signal as compared by the first comparator and a magnitude of the second reference signal as compared by the second comparator.

16. The skin contact detector according to claim 15, wherein the output signal generator produces the output in response to the trigger signal being applied by the signal generator to the output signal generator.

17. A personal care appliance comprising a skin contact detector for detecting contact with a probe with skin, said skin contact detector comprising:
- a signal generator configured to generate an electric trigger signal;
- a reference circuit including a capacitance ($C_{REF}$) and a resistance ($RP_{REF}$) configured to represent a model capacitance and resistance properties of the skin to be contacted by the probe, said reference circuit being adapted to produce a reference signal at a reference output of the reference circuit in response to the trigger signal being applied by the signal generator to a reference input of the reference circuit;
- a skin contact circuit adapted to produce a skin response signal at a skin contact output of the skin contact circuit in response to the trigger signal being applied by the signal generator to a skin contact input of the skin contact circuit, said skin response signal being representative of any variations of a skin capacitance and a skin resistance electrically applied by the probe to the skin contact circuit; and
- a comparator adapted to compare the skin response signal at the skin contact output of the skin contract circuit with the reference signal at the reference output of the reference circuit and to generate a predetermined output signal indicating skin contact by the probe when at least one of:
  - (i) the skin response signal simultaneously indicates the skin capacitance is larger than the capacitance ($C_{REF}$) of the reference circuit and the skin resistance is smaller than the resistance ($RP_{REF}$) of the reference circuit, or
  - (ii) the skin response signal simultaneously indicates the skin capacitance is smaller than the capacitance ($C_{REF}$) of the reference circuit and the skin resistance is larger than the resistance ($RP_{REF}$) of the reference circuit.

18. The personal care appliance according to claim 17, further comprising:
- an output signal generator adapted to produce an output indicating whether the comparator is generating the predetermined output signal indicating skin contact by the probe.

19. The personal care appliance according to claim 18, wherein the output signal generator produces the output in response to the trigger signal being applied by the signal generator to the output signal generator.

20. A skin contact detector for detecting contact of a plurality of probes with skin, said skin contact detector comprising:
- a plurality of skin contact detector circuits, each skin contact detector circuit including:
  - a signal generator configured to generate an electric trigger signal;
  - a reference circuit including a capacitance ($C_{REF}$) and a resistance ($RP_{REF}$) configured to represent a model of capacitance and resistance properties of the skin to be contacted by one of the plurality of probes, said reference circuit being adapted to produce a reference signal at a reference output of the reference circuit in response to the trigger signal being applied by the signal generator to a reference input of the reference circuit;
  - a skin contact circuit adapted to produce a skin response signal at a skin contact output of the skin contract circuit in response to the trigger signal being applied by the signal generator to a skin contact input of the skin contact circuit, said skin response signal being representative of any variations of a skin capacitance and a skin resistance electrically applied by the one of the plurality of probes to the skin contact circuit; and
  - a comparator adapted to compare the skin response signal at the skin contact output of the skin contact circuit with the reference signal at the reference output of the reference circuit and to generate a predetermined output signal indicating skin contact by the one of the plurality of probes when at least one of:
    - (i) the skin response signal simultaneous indicates the skin capacitance is larger than the capacitance ($C_{REF}$) of the reference circuit and the skin resistance is smaller than the resistance ($RP_{REF}$) of the reference circuit, or
    - (ii) the skin response signal simultaneously indicates the skin capacitance is smaller than the capacitance ($C_{REF}$) of the reference circuit and the skin resistance is larger than the resistance ($RP_{REF}$) of the reference circuit; and
- an output signal generator adapted to produce an output indicating whether at least one of the comparators are generating at least one of the predetermined output signals indicating skin contact by at least one of the plurality of probes.

\* \* \* \* \*